(12) United States Patent
Yi

(10) Patent No.: US 11,806,313 B2
(45) Date of Patent: Nov. 7, 2023

(54) ABIRATERONE ACETATE CONTAINING COMPOSITION AND APPLICATION THEREOF

(71) Applicant: Hunan Huize Biopharma S & T Co., Ltd, Hunan (CN)

(72) Inventor: Mulin Yi, Hunan (CN)

(73) Assignee: HUNAN HUIZE BIOPHARMA S&T CO., LTD., Hunan (CN)

( * ) Notice: Subject to any disclaimer, the term of this patent is extended or adjusted under 35 U.S.C. 154(b) by 0 days.

(21) Appl. No.: 18/064,587

(22) Filed: Dec. 12, 2022

(65) Prior Publication Data

US 2023/0181465 A1 Jun. 15, 2023

(30) Foreign Application Priority Data

Dec. 15, 2021 (CN) .......................... 202111532017.8
Jan. 17, 2022 (CN) .......................... 202210049441.5

(51) Int. Cl.
| | | |
|---|---|---|
| *A61K 9/107* | (2006.01) | |
| *A61P 15/00* | (2006.01) | |
| *A61P 35/00* | (2006.01) | |
| *A61K 9/48* | (2006.01) | |
| *A61K 31/58* | (2006.01) | |
| *A61K 47/14* | (2017.01) | |
| *A61K 47/44* | (2017.01) | |

(52) U.S. Cl.
CPC .......... *A61K 9/1075* (2013.01); *A61K 9/4858* (2013.01); *A61K 31/58* (2013.01); *A61K 47/14* (2013.01); *A61K 47/44* (2013.01); *A61P 15/00* (2018.01); *A61P 35/00* (2018.01)

(58) Field of Classification Search
CPC ........ A61K 31/58; A61K 47/10; A61K 47/14; A61K 47/44; A61K 9/1075; A61K 9/4858; A61P 13/08; A61P 15/00; A61P 35/00

See application file for complete search history.

(56) References Cited

FOREIGN PATENT DOCUMENTS

| CN | 102961358 | 3/2013 | | |
|---|---|---|---|---|
| CN | 103813794 | 5/2014 | | |
| CN | 105055314 | 11/2015 | | |
| CN | 105535979 | 5/2016 | | |
| CN | 106692051 | 5/2017 | | |
| CN | 106821977 | 6/2017 | | |
| CN | 107073127 | 8/2017 | | |
| CN | 107278152 | 10/2017 | | |
| CN | 107468650 | 12/2017 | | |
| CN | 110538150 | 12/2019 | | |
| CN | 110753545 | 2/2020 | | |
| CN | 111012745 | 4/2020 | | |
| CN | 113456588 | 10/2021 | | |
| CN | 113616614 | 11/2021 | | |
| CN | 113750032 | 12/2021 | | |
| EP | 3854384 | 7/2021 | | |
| EP | 4035657 | 8/2022 | | |
| TW | 201513896 | 4/2016 | | |
| WO | WO 2014009434 | 1/2014 | | |
| WO | WO 2014145813 | 9/2014 | | |
| WO | WO 2015193380 | 12/2015 | | |
| WO | WO 2018191141 | 10/2018 | | |
| WO | 2021/057042 A1 | * | 4/2021 | ............ A61K 31/58 |
| WO | WO 2021057042 | 4/2021 | | |

OTHER PUBLICATIONS

Boleslayska et al., "Bioavailability Enhancement and Food Effect Elimination of Abiraterone Acetate by Encapsulation in Surfactant-Enriched Oil Marbles", *The AAPS Journal*, vol. 22, 2020, 12 pages.
Extended European Search Report issued in corresponding European application No. 22212792.0 dated May 4, 2023.
Extended European Search Report issued in corresponding European application No. 20867834.2 dated Oct. 19, 2022.
International Search Report and Written Opinon issued in corresponding International application PCT/CN2020/090866 dated Aug. 13, 2020.
Office Action issued in corresponding Chinese Application No. 2021030302059080 dated Mar. 8, 2021.
Office Action issued in corresponding Japanese Application No. 2022198156, dated Apr. 11, 2023.
Penjuri et al., "Development of Self Emulsifying Formulations of Poorly Soluble Naproxen for Enhanced Drug Delivery", *Recent Patents on Drug Delivery & Formulation*, vol. 10, pp. 235-244, 2016.
Pouton, "Formulation of self-emulsifying drug delivery systems", *Advanced Drug Delivery Reviews*, vol. 245, pp. 47-58, 1997.
Ren, et al., "Clinical progress of abiraterone in the treatment of metastatic prostatic cancer", *Jingyixingye Science and Technology*, 2016, pp. 205-212 (English abstract provided).

* cited by examiner

*Primary Examiner* — Jean P Cornet
(74) *Attorney, Agent, or Firm* — NORTON ROSE FULBRIGHT US LLP

(57) ABSTRACT

Disclosed is a self-microemulsion system for loading abiraterone acetate, and a composition and an application thereof. The self-microemulsion system for loading abiraterone acetate has excellent solubility and stability for abiraterone acetate, and the composition formed by dissolving abiraterone acetate in this system can significantly reduce the effect of food on the absorption of abiraterone acetate, and reduce the differences between preprandial administration and postprandial administration, thus making it possible to take the medicament on both an empty and a full stomach and reducing the limitation for the time of taking medicament.

11 Claims, 7 Drawing Sheets

ABIRATERONE ACETATE CONTAINING COMPOSITION AND APPLICATION THEREOF

FIELD OF THE INVENTION

The invention relates to the technical field of abiraterone acetate preparations, particularly to a self-microemulsion system for loading abiraterone acetate, and a composition and application thereof.

BACKGROUND OF THE INVENTION

Abiraterone acetate is a white to off-white, non-hygroscopic crystalline powder, which has a chemical name of (3β)-17-(3-pyridyl)androsta-5,16-dien-3-yl acetate and has a molecular formula of $C_{26}H_{33}NO_2$. Abiraterone acetate can be converted in vivo to an inhibitor against androgen biosynthesis, namely abiraterone, which inhibits 17α-hydroxylase/C17,20-lyase (CYP17). It can be administered in combination with prednisone for the treatment of patients with metastatic castration-resistant prostate cancer (CRPC) who have previously received chemotherapy involving docetaxel. However, abiraterone acetate is a lipophilic compound with an octanol-water partition coefficient of 5.12 (Log P) and a pKa of aromatic nitrogen of 5.19. Abiraterone acetate is almost insoluble in water (less than 0.01 mg/ml), has a poor permeability, belongs to BCS class IV drug, and has a very low bioavailability when administered orally.

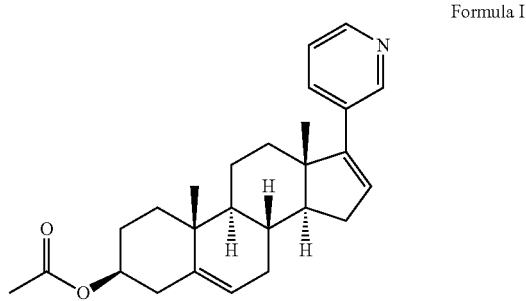

Formula I

Zytiga, the innovator drug of abiraterone acetate, is a tablet. Each tablet of Zytiga contains 250 mg of abiraterone acetate and inactive ingredients comprising: colloidal silicon dioxide, croscarmellose sodium, lactose monohydrate, magnesium stearate, microcrystalline cellulose, polyvidone, and sodium dodecylsulfate. The oral bioavailability of Zytiga is very low (less than 10%). A single dosage of Zytiga is up to 1000 mg, but only less than 10% of the drug can work.

Moreover, the absorption of abiraterone acetate is largely affected by food, and the commercially available preparations need to be taken only at a specific time period before meals. The package insert of Zytiga emphasizes that the systemic exposure of abiraterone acetate is increased when it is administered together with food. When abiraterone acetate is given together with a low-fat diet (7% fat, 300 calories), $C_{max}$ and $AUC_{0-\infty}$ of abiraterone increase about 7 times and 5 times, respectively. When abiraterone acetate is given together with a high-fat diet (57% fat, 825 calories), $C_{max}$ and $AUC_{0-\infty}$ increase about 17 times and 10 times, respectively. Taking into account the normal variation in the content and composition of diet, it may result in an increased and highly variable exposure when abiraterone acetate is taken together with diet. Therefore, in order to control the abiraterone concentration in plasma, dose must be taken on an empty stomach and, no food should be taken for at least two hours before and at least 1 hour after taking the said dose. Accordingly, although abiraterone acetate has a good treatment effect on advanced prostate cancer orally, its natures of low solubility and poor permeability have brought obstacles to preparation designing.

Sun Pharmaceutical Industries Ltd., India provides an modified abiraterone acetate tablet, namely Yonsa, by Solu-Matrix microparticle technology, which can promote the dissolution of abiraterone acetate and increases the oral bioavailability of the innovator drug Zytiga by 1 times. Although the dosage of Yonsa is reduced to 500 mg, it only changes the crystal form and size of the drug and increases the drug dissolution rate, and fails to increase the permeability of abiraterone acetate through gastrointestinal epithelial cells, and thus the oral bioavailability of Yonsa remains very low.

Patent document CN107278152A relates to a complex of abiraterone acetate, preparation method thereof and pharmaceutical composition containing the same. The complex comprises 5-40 wt. % of abiraterone acetate, 5-80 wt. % of polyvinyl caprolactam-polyvinyl acetate-polyethylene glycol graft copolymer, and 0.1-50 wt. % of sodium deoxycholate. It can reduce the effect of food and thus eliminate the requirement of taking medicament on an empty stomach. It can also increase the oral bioavailability by 5 times. However, the preparation process of the complex is complicated. Patent document WO2021057042 discloses a self-microemulsion composition of abiraterone acetate, and preparation method and application thereof. Said composition comprises 5-20 wt. % of abiraterone acetate, 20-50 wt. % of an oil phase, 20-60 wt. % of an emulsifier, and 20-80 wt. % of a co-emulsifier. The pharmaceutical composition needs strong mechanical stirring to be completely dissolved during the dissolution process, and the bioavailability after oral administration still needs to be improved.

SUMMARY OF THE INVENTION

In view of the deficiencies of the prior art, an object of the present invention is to provide a self-microemulsion system for loading abiraterone acetate, and a method for preparing the abiraterone acetate composition using the system and application thereof. The self-microemulsion system for loading abiraterone acetate of the present invention has an excellent solubility and stability to abiraterone acetate, and the composition formed by dissolving abiraterone acetate in the system can significantly reduce the effect of food on abiraterone acetate absorption, reduce the difference between preprandial and postprandial administering, such that the medicament can be taken on both an empty stomach and a full stomach, thus reducing the time limit for taking the medicament.

To achieve the above object, the technical solutions adopted in the present invention are as follows.

According to the first embodiment of the present invention, a self-microemulsion system for loading abiraterone acetate is provided.

The self-microemulsion system for loading abiraterone acetate comprises an oil phase and an emulsion phase, wherein the ratio of the weight percentages of the oil phase and the emulsion phase is 30%-38%:62%-70%, preferably 31%-35%:65%-69%, more preferably 32%-34%:66%-68%. For example, the ratio can be any one of 30%:70%, 31%:69%, 32%:68%, 32.5%:67.5%, 33%:67%, 33.5%:66.5%, 34%:66%, 34.5%:65.5%, and 35%:65%.

Preferably, the oil phase comprises glycerol monolinoleate (CC) and medium chain triglyceride (MCT).

Preferably, the emulsion phase comprises PEG-40 hydrogenated castor oil (RH40) and 2-(2-ethoxyethoxy)ethanol (HP).

Preferably, the weight ratio of glycerol monolinoleate to medium chain triglyceride in the oil phase is 2.5-3.63:1.

Preferably, the weight ratio of PEG-40 hydrogenated castor oil to 2-(2-ethoxyethoxy)ethanol in the emulsion phase is 1:2.25-2.5.

Preferably, the weight ratio of glycerol monolinoleate to medium chain triglyceride in the oil phase is 2.8-3.5:1.

Preferably, the weight ratio of PEG-40 hydrogenated castor oil to 2-(2-ethoxyethoxy)ethanol in the emulsion phase is 1:2.28-2.45.

Preferably, the weight ratio of the glycerol monolinoleate to the medium chain triglyceride in the oil phase is 3.0-3.4:1.

Preferably, the weight ratio of PEG-40 hydrogenated castor oil to 2-(2-ethoxyethoxy)ethanol in the emulsion phase is 1:2.25-2.4.

In the self-microemulsion system comprising the oil phase and the emulsion phase of the present invention, the ratio of 2-(2-ethoxyethoxy)ethanol (HP) to PEG-40 hydrogenated castor oil (RH40) increases with the proportion of the emulsion phase (wt. %, based on the total weight of the self-microemulsion system comprising the oil phase and the emulsion phase). Preferably, when the proportion of the emulsion phase increases or decreases by 1 wt. %, the ratio of 2-(2-ethoxyethoxy)ethanol (HP) to PEG-40 hydrogenated castor oil (RH40) increases or decreases by 0.05 correspondingly. That is to say, when the proportion of the emulsion phase steps up from 65 wt. % to 70 wt. % (each step is 1 wt. %), the ratio of 2-(2-ethoxyethoxy)ethanol (HP) to PEG-40 hydrogenated castor oil (RH40) steps up from 2.25 to 2.5 (each step is 0.05). Conversely, when the proportion of the emulsion phase steps down from 70 wt. % to 65 wt. % (each step is 1 wt. %), then the ratio of 2-(2-ethoxyethoxy)ethanol (HP) to PEG-40 hydrogenated castor oil (RH40) also steps down from 2.5 to 2.25 (each step is 0.05).

In the present invention, the self-microemulsion system can be obtained through homogeneously mixing glycerol monolinoleate, medium chain triglyceride, PEG-40 hydrogenated castor oil, 2-(2-ethoxyethoxy)ethanol, and the like in proportion. For example, the self-microemulsion system can be obtained through firstly mixing glycerol monolinoleate and medium chain triglyceride in proportion to obtain an oil phase; secondly mixing PEG-40 hydrogenated castor oil and 2-(2-ethoxyethoxy)ethanol in proportion to obtain an emulsion phase, and lastly mixing the oil phase and the emulsion phase.

According to the second embodiment of the present invention, an abiraterone acetate-containing composition is provided.

The abiraterone acetate-containing composition comprises abiraterone acetate and the self-microemulsion system as described in the first embodiment, wherein the ratio of weight percentages of abiraterone acetate and self-microemulsion system is 4.3-4.8%:95.2-95.7%, preferably 4.4-4.6%:95.4-95.6%. For example, the ratio of weight can be any one of 4.3%:95.7%, 4.4%:95.6%, 4.5%:95.5%, 4.6%:95.4%, 4.7%:95.3%, and 4.8%:95.2%.

Preferably, the content of each component of the composition is as follows.

Abiraterone acetate: 4.3-4.8 wt. %, preferably 4.4-4.6 wt. %, for example any one of 4.3 wt. %, 4.4 wt. %, 4.5 wt. %, 4.6 wt. %, 4.7 wt. %, and 4.8 wt. %.

Glycerol monolinoleate: 21.4-26.2 wt. %, preferably 22.0-26.0 wt. %, for example any one of 21 wt. %, 21.2 wt. %, 21.4 wt. %, 21.6 wt. %, 21.8 wt. %, 22 wt. %, 22.2 wt. %, 22.5 wt. %, 22.8 wt. %, 23 wt. %, 23.3 wt. %, 23.5 wt. %, 23.8 wt. %, 24 wt. %, 24.3 wt. %, 24.5 wt. %, 24.8 wt. %, 25 wt. %, 25.2 wt. %, 25.4 wt. %, 25.6 wt. %, 25.8 wt. %, 26 wt. %, and 26.2 wt. %.

Medium chain triglyceride: 6.2-9.6 wt. %, preferably 6.8-8.8 wt. %, for example any one of 6.2 wt. %, 6.3 wt. %, 6.4 wt. %, 6.5 wt. %, 6.6 wt. %, 6.7 wt. %, 6.8 wt. %, 6.9 wt. %, 7.0 wt. %, 7.1 wt. %, 7.2 wt. %, 7.3 wt. %, 7.4 wt. %, 7.5 wt. %, 7.6 wt. %, 7.7 wt. %, 7.8 wt. %, 7.9 wt. %, 8.0 wt. %, 8.2 wt. %, 8.3 wt. %, 8.4 wt. %, 8.5 wt. %, 8.6 wt. %, 8.7 wt. %%, 8.8 wt. %, 8.9 wt. %, 9.0 wt. %, 9.1 wt. %, 9.2 wt. %, 9.3 wt. %, 9.4 wt. %, 9.5 wt. %, and 9.6 wt. %.

PEG-40 hydrogenated castor oil: 17.7-19.7 wt. %, preferably 18.5-19.5 wt. %, for example any one of 17.7 wt. %, 17.8 wt. %, 17.9 wt. %, 18.0 wt. %, 18.1 wt. %, 18.2 wt. %, 18.3 wt. %, 18.4 wt. %, 18.5 wt. %, 18.6 wt. %, 18.7 wt. %, 18.8 wt. %, 18.9 wt. %, 19.0 wt. %, 19.1 wt. %, 19.2 wt. %, 19.3 wt. %, 19.4 wt. %, 19.5 wt. %, 19.6 wt. %, and 19.7 wt. %.

2-(2-ethoxyethoxy)ethanol: 42.8-47.8 wt. %, preferably 43.0-47.2 wt. %, for example any one of 42.8 wt. %, 43 wt. %, 43.2 wt. %, 43.3 wt. %, 43.4 wt. %, 43.5 wt. %, 43.6 wt. %, 43.7 wt. %, 43.8 wt. %, 44 wt. %, 44.3 wt. %, 44.5 wt. %, 44.8 wt. %%, 45 wt. %, 45.3 wt. %, 45.5 wt. %, 45.8 wt. %, 46.1 wt. %, 46.5 wt. %, 46.8 wt. %, 47.1 wt. %, 47.5 wt. %, and 47.8 wt. %.

Preferably, the composition further comprises optional antioxidants and/or preservatives comprising 0.005%-0.1% of the total weight of the composition. In the context of present disclosure, an "optional" ingredient means the ingredient can be comprised or not comprised in the composition.

In the present invention, the abiraterone acetate-containing composition can be obtained through dissolving abiraterone acetate in the self-microemulsion system in proportion, and then optionally adding an antioxidant and/or preservative, and then homogeneously mixing the mixture. For example, the composition can be obtained through mixing glycerol monolinoleate, medium chain triglyceride, PEG-40 hydrogenated castor oil (at room temperature or under heating) in proportion, then adding abiraterone acetate and stirring in dark place, and finally adding 2-(2-ethoxyethoxy)ethanol and optional an antioxidant and/or preservative and mixing them homogeneously.

According to the third embodiment of the present invention, an abiraterone acetate preparation is provided.

The abiraterone acetate preparation comprises a solid preparation and a liquid preparation. The solid preparation comprises, but is not limited to, one or more of tablet, capsule, granule, powder, dripping pill, and film. The liquid preparation comprises, but is not limited to, one or more of injection, soft capsule, ointment, suppository, and aerosol.

Preferably, the solid preparation is obtained by one or more steps of crushing, sieving, mixing, granulating, and tableting the content(s) and adjuvant(s). The adjuvant(s) is selected from one or more of filler, adsorbent, binder, lubricant, dispersant, disintegrant, wetting agent, spice, and colorant. The content(s) is the self-microemulsion system described in the first embodiment and abiraterone acetate, or the abiraterone acetate-containing composition described in the second embodiment.

The liquid preparation composes of content(s) and auxiliary agent(s). The auxiliary agent is selected from one or more of preservative, stabilizer, antioxidant, aromatizer, osmotic pressure regulator, and flavoring agent. The content is the self-microemulsion system described in the first embodiment and abiraterone acetate, or the abiraterone acetate-containing composition described in the second embodiment.

In the present invention, the abiraterone acetate preparation can be obtained by those skilled in the art according to the preparation method of conventional preparations in the art. For example, it can be obtained through preparing the abiraterone acetate-containing composition according to the aforementioned process; and sealing the abiraterone acetate-containing composition in soft capsules or hard capsules. Preferably, each capsule contains 0.5-1 mL of the abiraterone acetate-containing composition.

In the present invention, the concentration of abiraterone acetate in the abiraterone acetate-containing composition can range from 50-100 mg/mL, and the single oral dosage can be 75-100 mg. The abiraterone acetate can form an O/W nano emulsion with a high clarity, an uniform particle size of less than 250 nm, and a stable nature spontaneously when mixing with water, biologically relevant media (such as SGF and FassiF medium) or gastrointestinal fluid. The content(s) can exist as a stable solution when stored at room temperature. Furthermore, the self-microemulsion composition of the present invention is stable even under conditions of influencing factors (e.g. at 30° C.±2° C., at 4° C., addition of 10 wt. % of water based on the total weight of the composition, addition of 15 wt. % of water based on the total weight of the composition).

According to the fourth embodiment of the present invention, a pharmaceutical composition is provided.

The pharmaceutical composition comprises the abiraterone acetate-containing composition described in the second embodiment or the abiraterone acetate preparation described in the third embodiment, and prednisone. That is, pharmaceutical composition comprises the combination of abiraterone acetate-containing composition and prednisone, or the combination of abiraterone acetate preparation and prednisone.

According to the fifth embodiment of the present invention, an application of the abiraterone acetate-containing composition described in the second embodiment or the abiraterone acetate preparation described in the third embodiment or the pharmaceutical composition described in the fourth embodiment, wherein the abiraterone acetate-containing composition described in the second embodiment or the abiraterone acetate preparation described in the third embodiment or the pharmaceutical composition described in the fourth embodiment is used in the manufacture of a pharmaceutical preparation for treating prostate cancer.

Preferably, the prostate cancer is selected from one or both of metastatic castration-resistant prostate cancer and metastatic high-risk castration-sensitive prostate cancer. Generally, the medicament according to the present invention can be administered either before meal or after meal.

In the prior art, abiraterone acetate, as a BSC class IV drug, has a low solubility and a low permeability. In the process of developing dosage forms, it is necessary to address not only the solubility of abiraterone, but more importantly, the transmembrane problem of abiraterone in the absorption process. The currently existing dosage forms of abiraterone acetate can effectively solve the problems of solubility and dissolution of abiraterone acetate, but fail to solve the problem of the transmembrane and absorption of the medicament in vivo, and thus the bioavailability is not effectively improved. Moreover, the existing dosage forms also fail to effectively solve the problem of precipitation of abiraterone acetate due to moisture absorption, resulting in its low stability. Further, the self-microemulsion systems for loading abiraterone acetate in the prior art do not reasonably control the ratio of the oil phase and the emulsion phase, and consequently the amount of 2-(2-ethoxyethoxy)ethanol in the emulsion phase in either too much (which can lead to toxic and side effects) or too little (which makes it hard or unable to form a microemulsion).

In the present invention, the abiraterone acetate-containing composition is a solution system, which will, after oral administration, spontaneously disperse to form an O/W nanoemulsion with a high clarity, a uniform particle size and a stable nature in the presence of gastrointestinal fluid under gastrointestinal peristalsis. The nanoemulsion has a small particle size, which can promote drug dissolution, increase the membrane permeability of abiraterone in vivo, and increase the permeability to intestinal epithelial cells, thereby significantly promoting absorption and significantly improving drug bioavailability. The abiraterone acetate-containing composition of the present invention can also significantly reduce the effect of food on the absorption of abiraterone acetate and reduce the difference between preprandial and postprandial administering, such that it can be taken on both an empty stomach and a full stomach, and the time limit for taking the medicament is reduced.

In the present invention, the provided self-microemulsion system can be used as a carrier for a medicament that is hydrophobic, hard to absorb or easy to hydrolyze. While improving the solubility of abiraterone acetate at room temperature, the formed uniform and stable abiraterone acetate-containing medicament system can spontaneously disperse to form a nanoemulsion after entering the body, which can effectively solve the problem of transmembrane and absorption of abiraterone acetate in vivo. Through in-depth research, it is found that the oral bioavailability of the abiraterone acetate-containing composition prepared in the present invention is greatly improved, and the stability in a humid or excessively humid environment is also excellent. Comparing with microemulsion, the self-emulsification solution has a higher stability and can meet the requirements for long-term storage, and it can also be directly packed into soft capsules or hard capsules.

Compared with the prior art, the beneficial technical effects of the present invention are as follows.

1. In the present invention, the oil phase and the emulsion phase are prepared by selecting specific raw materials in a specific ratio, and then the self-microemulsion system for loading abiraterone acetate is obtained by mixing the oil phase and the emulsion phase in a specific ratio. The self-microemulsion system has a high solubility and a strong stability to abiraterone acetate, and spontaneously disperses to form O/W nanoemulsion with a high clarity, a uniform particle size and a stable nature under gastrointestinal peristalsis. The membrane permeability of abiraterone acetate in vivo is greatly improved, and the penetration to intestinal epithelial cells is increased, such that the absorption and the drug bioavailability are significantly promoted.

2. The abiraterone acetate-containing composition of present invention is prepared with abiraterone acetate and an inventive self-microemulsion system, which can significantly reduce the effect of food on the absorption of abiraterone acetate and reduce the difference between preprandial and postprandial administering, such that the medicament can be taken on both an empty stomach and a full stomach, reducing the time limit for taking the medicament.

DETAILED DESCRIPTION

The technical solutions of the present invention are illustrated below by way of example, and the scope of the claimed protection of the present invention includes but is not limited to the following examples.

Experiment 1: Construction of Self-Microemulsion System

Glycerol monolinoleate (CC) and medium chain triglyceride (MCT) were mixed in different weight ratios (the weight ratios are 1:0, 1:1, 2:1, 1:2, 3:1, 1:3, 5:1, and 1:5) to obtain the oil phase. PEG-40 hydrogenated castor oil (RH40) and 2-(2-ethoxyethoxy)ethanol (HP) were mixed in different weight ratios (the weight ratios are 1:1, 2:1, 1:2, 3:1, and 1:3) to obtain the emulsion phase. Then, the oil phase and the emulsion phase were mixed in different weight ratios (the weight ratios are 9:1, 8:2, 7:3, 6:4, 5:5, 4:6, 3:7, 2:8, and 1:9) to obtain a mixed system. Ternary phase diagrams (see FIGS. 1-8) were obtained using a Karl Fischer method, and the loading performance of the mixed system to abiraterone acetate (API) was investigated.

Figure 1:
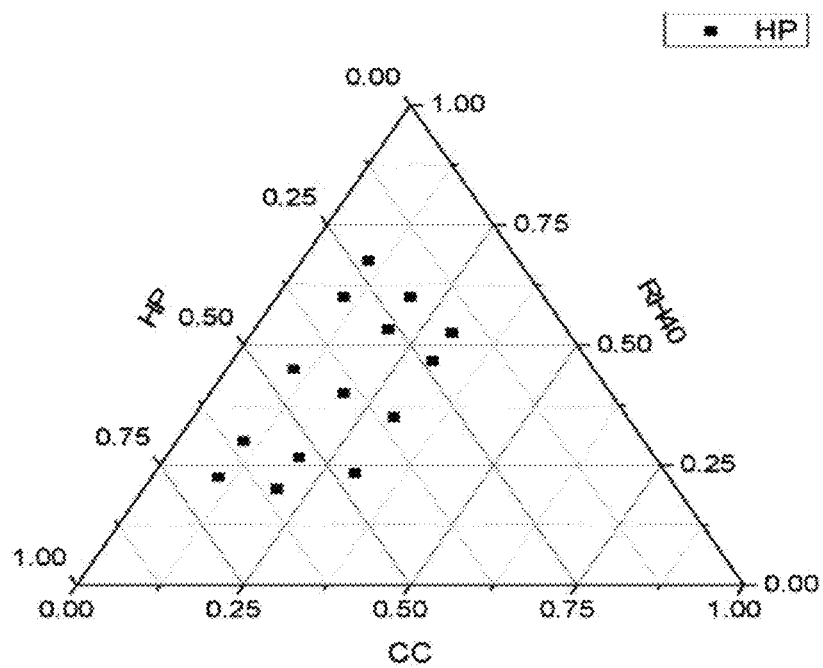
FIG. 1 is a ternary phase diagram drawn by proportionally adjusting the amounts of HP, RH40 and a mixture of (CC:MCT=1:0).
Figure 2:
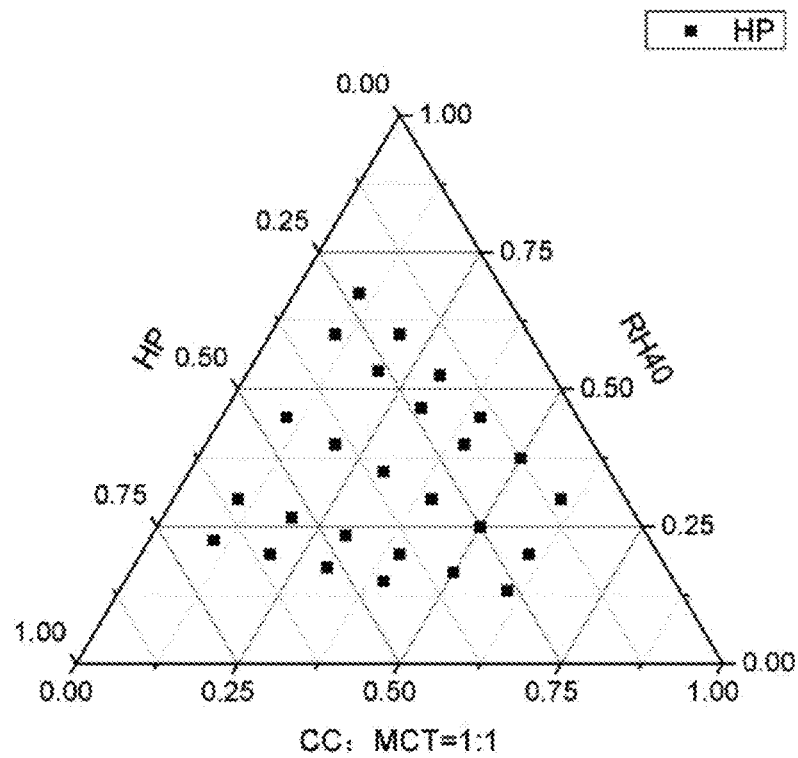
FIG. 2 is a ternary phase diagram drawn by proportionally adjusting the amounts of HP, RH40 and a mixture of (CC:MCT=1:1).
Figure 3:
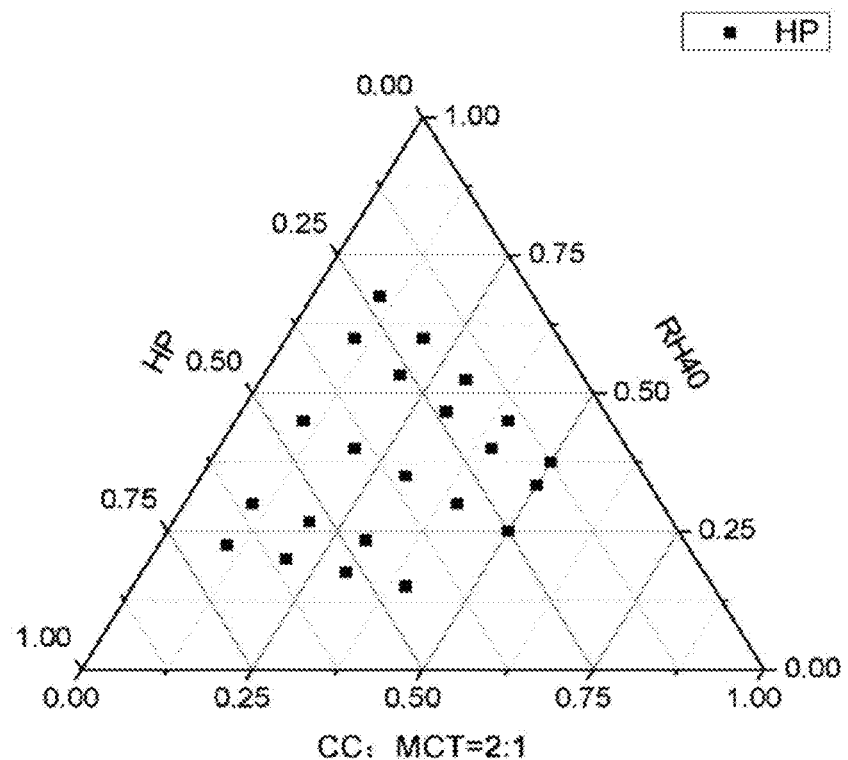
FIG. 3 is a ternary phase diagram drawn by proportionally adjusting the amounts of HP, RH40 and a mixture of (CC:MCT=2:1).
Figure 4:
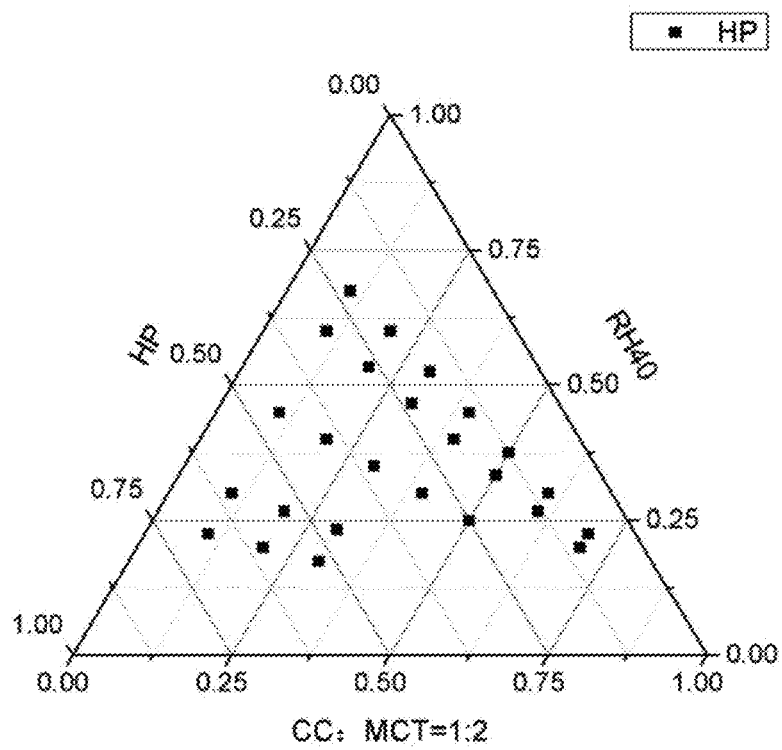
FIG. 4 is a ternary phase diagram drawn by proportionally adjusting the amounts of HP, RH40 and a mixture of (CC:MCT=1:2).
Figure 5:
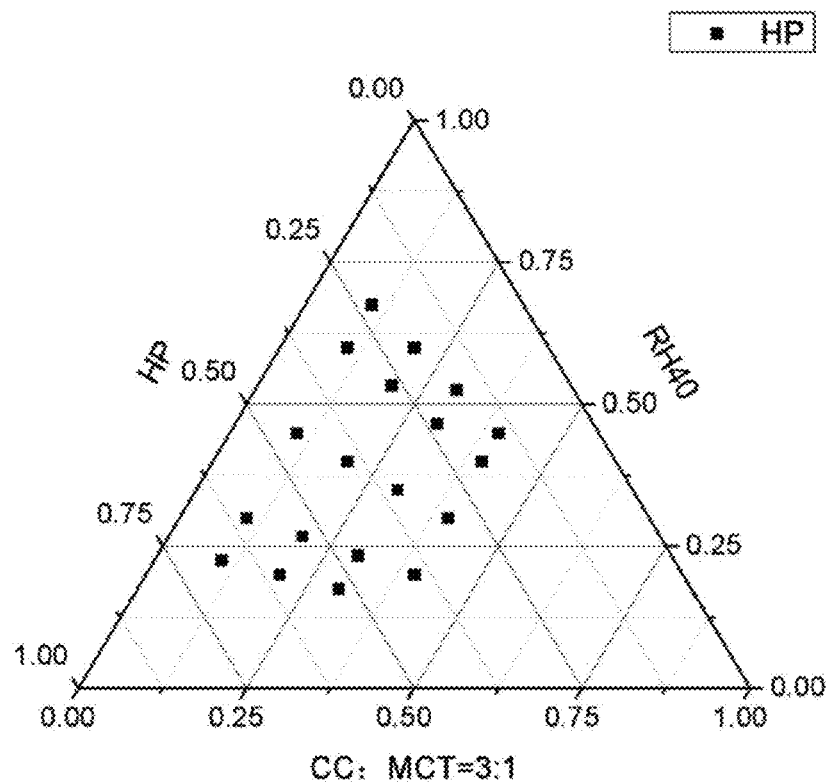
FIG. 5 is a ternary phase diagram drawn by proportionally adjusting the amounts of HP, RH40 and a mixture of (CC:MCT=3:1).
Figure 6:
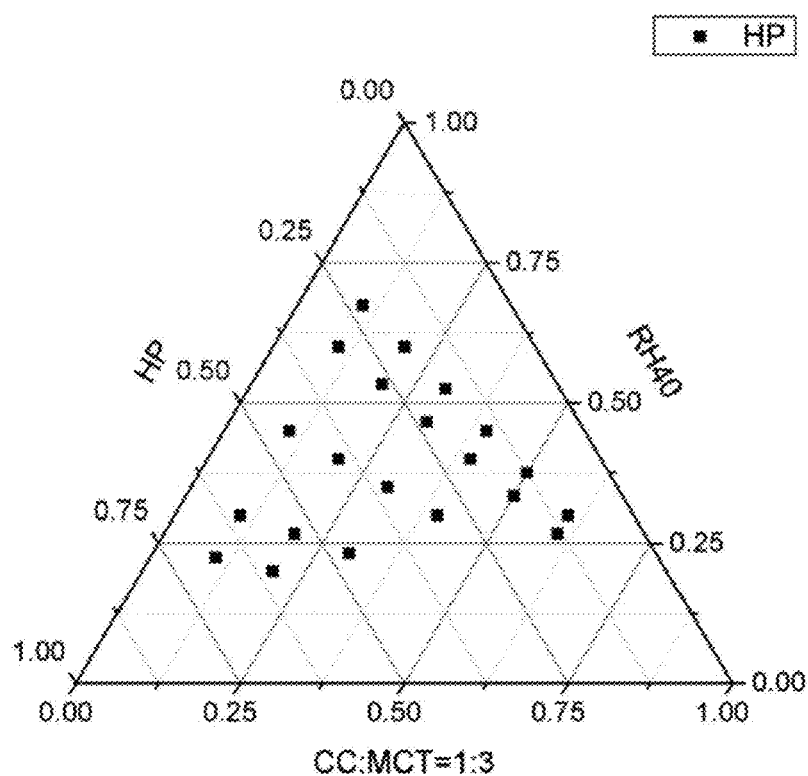
FIG. 6 is a ternary phase diagram drawn by proportionally adjusting the amounts of HP, RH40 and a mixture of (CC:MCT=1:3).
Figure 7:
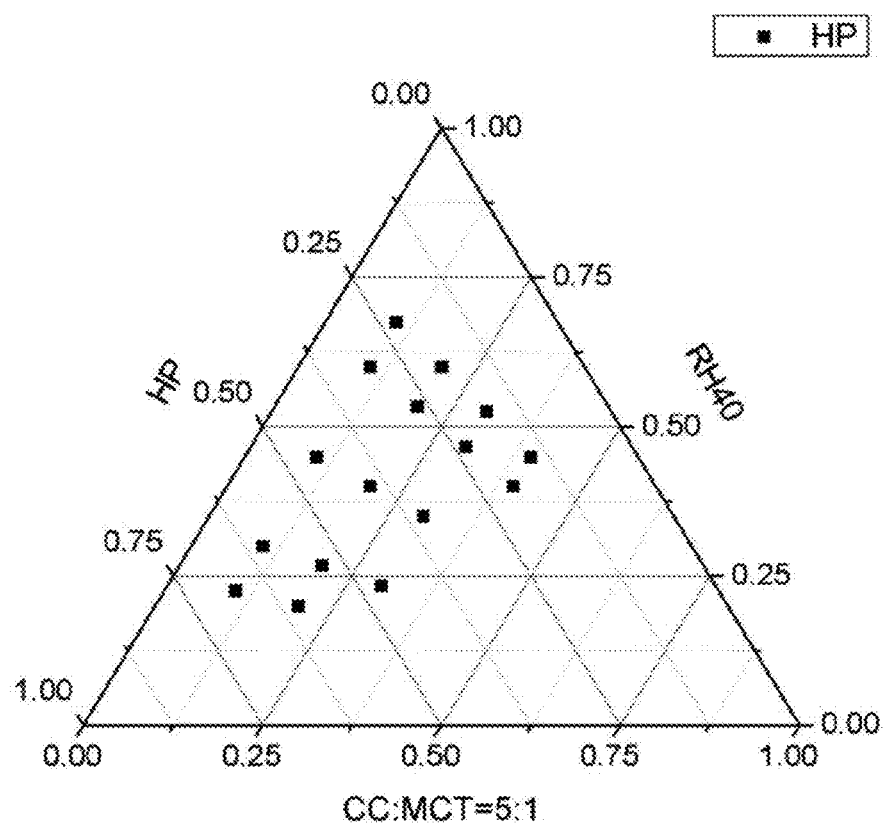
FIG. 7 is a ternary phase diagram drawn by proportionally adjusting the amounts of HP, RH40 and a mixture of (CC:MCT=5:1).
Figure 8:
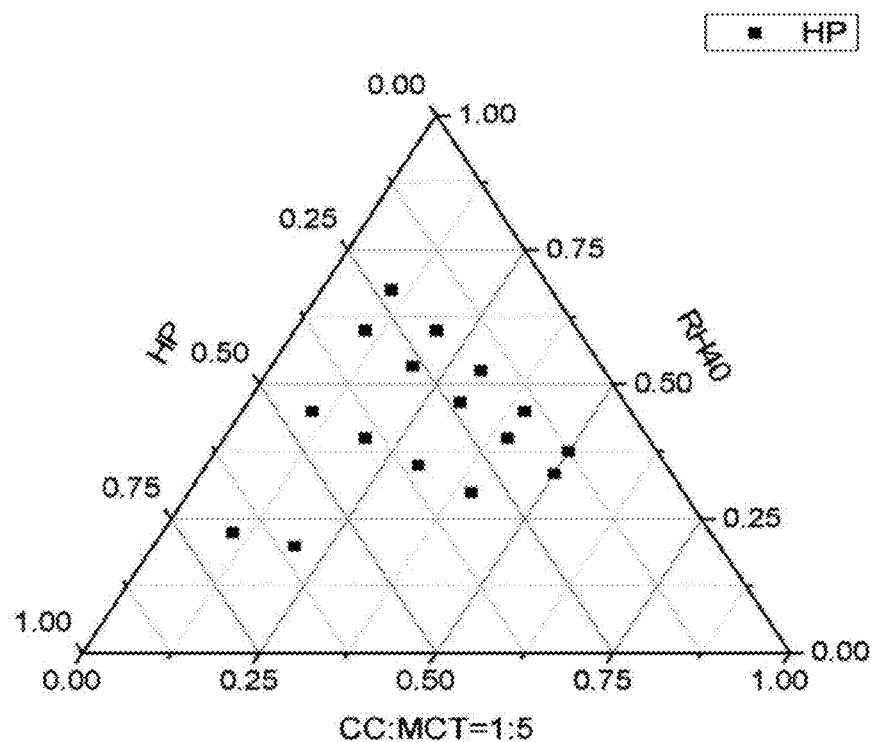
FIG. 8 is a ternary phase diagram drawn by proportionally adjusting the amounts of HP, RH40 and a mixture of (CC:MCT=1:5).
Figure 9:
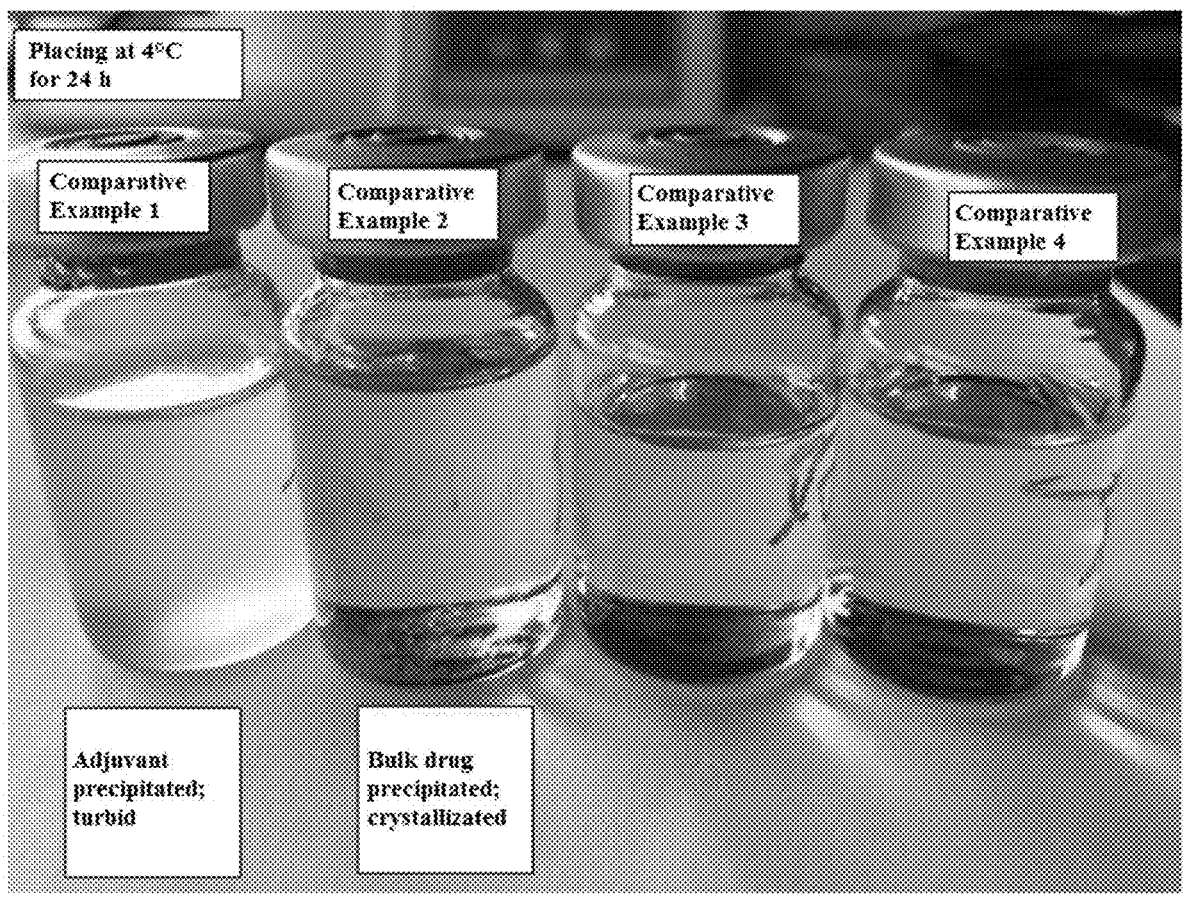
FIG. 9 shows the sample photos of abiraterone acetate-containing compositions of Comparative examples 1-4 after being placed at 4° C. for 24 h.
Figure 10:
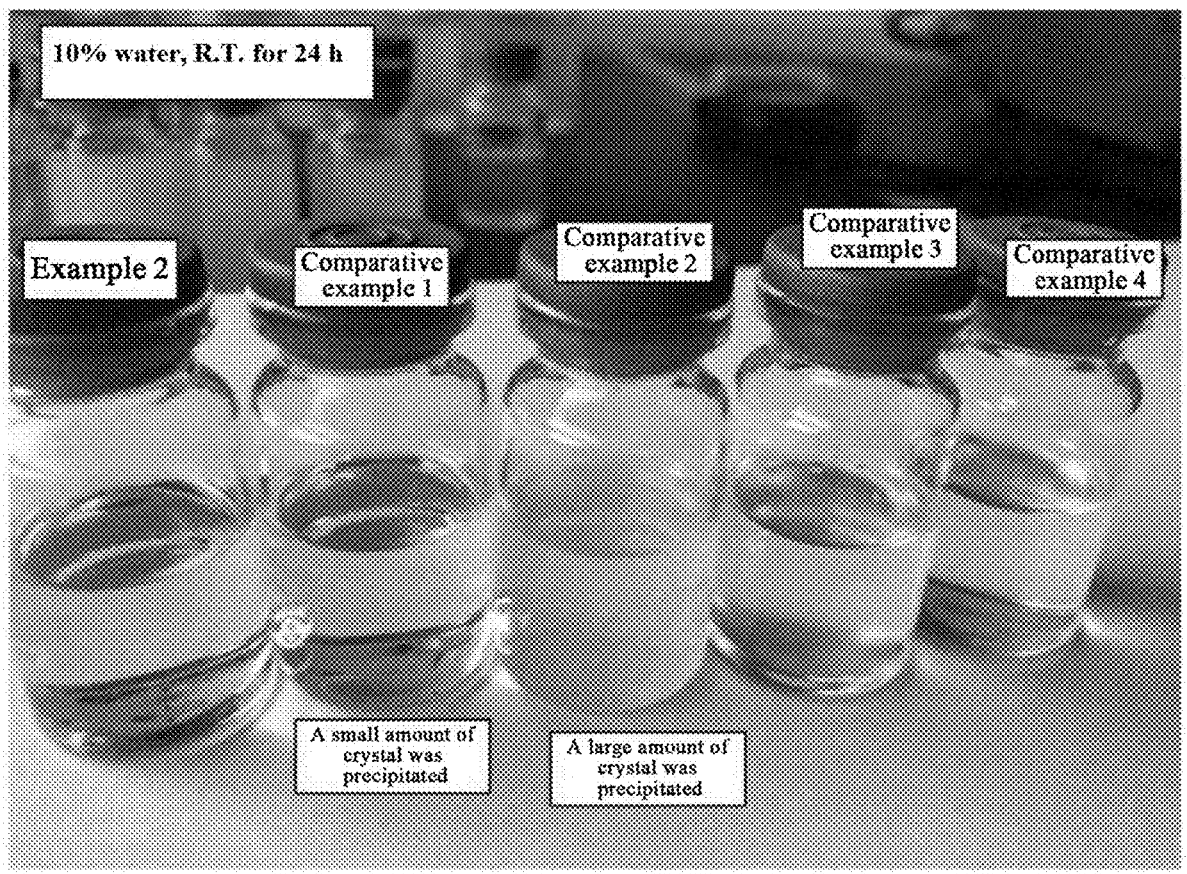
FIG. 10 shows the sample photos of abiraterone acetate-containing compositions of Example 2 and Comparative examples 1-4 after being placed at room temperature for 24 h with 10 wt. % of water added.
Figure 11:
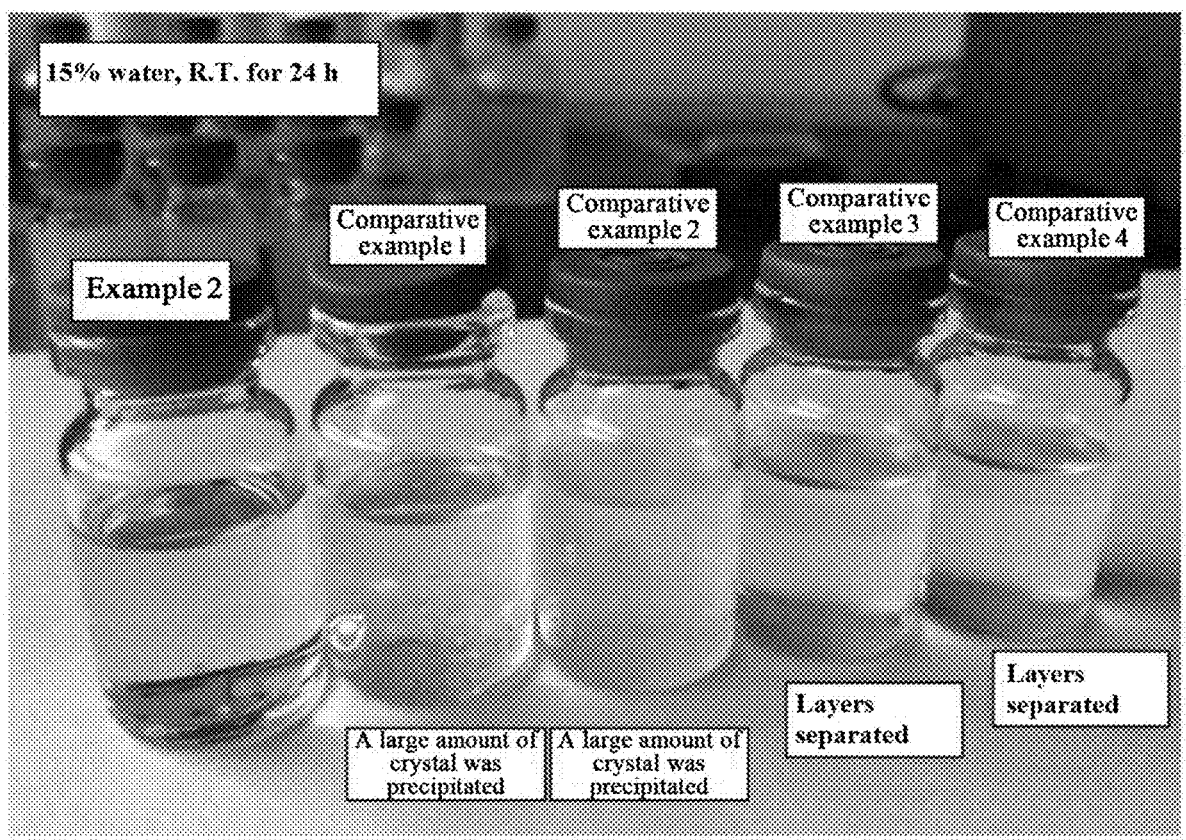
FIG. 11 shows the sample photos of abiraterone acetate-containing compositions of Example 2 and Comparative examples 1-4 after being placed at room temperature for 24 h with 15 wt. % of water added.

It can be seen from FIGS. 1-8 that, as the oil phase, the combination of glycerol monolinoleate and medium chain triglyceride is more effective than glycerol monolinoleate alone (See FIGS. 1-8, wherein FIG. 1 represents the ternary phase diagram when glycerol monolinoleate was used alone as the oil phase, and FIGS. 2-7 represent the ternary phase diagrams when the combination of glycerol monolinoleate and medium chain triglyceride in different weight ratios were used as the oil phase. It can be seen that the area of the microemulsion zone in FIG. 1 is the smallest. For example, referring to FIG. 1 and FIG. 2, when a combination of glycerol monolinoleate and medium chain triglyceride is used, microemulsion can still be achieved when the amount of oil phase is 50%, but the microemulsion state cannot be achieved when glycerol monolinoleate is used alone in the amount of 50%, no matter how the ratio of RH40 and HP is adjusted). Therefore, the self-microemulsion system of the present invention can choose the mixture of glycerol monolinoleate (CC) and medium chain triglyceride (MCT) as the oil phase. Besides, it is found through experiments that the solubility of abiraterone acetate in glycerol monolinoleate (CC) (25° C.) was about 62.9 mg/g, and the solubility in medium chain triglyceride (MCT) (25° C.) was about 28.4 mg/g. Accordingly, when glycerol monolinoleate and medium chain triglyceride are used in combination as the oil phase, in order to ensure a larger drug loading capacity, the amount of CC in the oil phase should be as much as possible, while the amount of MCT should be as little as possible. During the research, it was found that, when the amount and ratio of the emulsion phase were constant, the area of the microemulsification region in the ternary phase diagram gradually decreases as the ratio of amount of glycerol monolinoleate to medium chain triglyceride varying from 2:1 to 5:1 (the area where the microemulsion exists decreases with the area of the microemulsification region, and the small area renders the amount of adjuvants is restricted. This further leads a restriction on API loading, while also affects the self-emulsification effect of the self-microemulsion system). Furthermore, through further experiments and calculations, it was found that when the value of CC:MCT in the oil phase was 2.5-3.63:1 (preferably 2.8-3.5:1, more preferably 3.0-3.4:1), the loading of abiraterone acetate was excellent (an excessive amount of MCT will lead to a significant decrease in API loading, while too few MCT will lead to a small emulsification area), and the self-microemulsion system comprising the oil phase and emulsion phase can achieve a good self-emulsification effect.

Through experiments, it was found that using the combination of PEG-40 hydrogenated castor oil (RH40) and 2-(2-ethoxyethoxy)ethanol (HP) as the emulsion phase can obtain a better effect than using PEG-40 hydrogenated castor oil (RH40) alone, because 2-(2-ethoxyethoxy)ethanol (HP) can assist the emulsification and also reduce the amount of PEG-40 hydrogenated castor oil (RH40) and increase the loading capacity of abiraterone acetate. Through experiments, it was found that the solubility of abiraterone acetate in PEG-40 hydrogenated castor oil (RH40) (25° C.) was about 24.7 mg/g, and the solubility in 2-(2-ethoxyethoxy)ethanol (HP) (25° C.) was about 69.0 mg/g. When PEG-40 hydrogenated castor oil (RH40) and 2-(2-ethoxyethoxy)ethanol (HP) are used in combination as the emulsion phase, in order to ensure the emulsification effect of the self-microemulsion system and to ensure a large drug loading capacity, one should increase the amount of RH40 in the emulsion phase while also reduce the amount of HP as much as possible. During the research, it was found that, when the amount and ratio of the oil phase were constant, the area of the microemulsification region in the ternary phase diagram gradually decreases as the ratio of the amount of PEG-40 hydrogenated castor oil to 2-(2-ethoxyethoxy)ethanol varying from 1:1 to 1:3. Meanwhile, through further experiments, it was also found that when the ratio of RH40 to HP in the emulsion phase is 1:2.25-2.5, an well loading of abiraterone acetate and excellent self-emulsification of the self-microemulsion system composed of abiraterone acetate and the oil phase can be achieved, while the co-emulsifier (i.e., HP) was accommodated and shielded by the self-microemulsion system, producing almost no toxic and side effect.

In a preferred embodiment of the present invention, an oil phase was obtained by mixing CC and MCT according to weight ratio CC:MCT=3.38:1, and an emulsion phase was obtained by mixing RH40 and HP according to weight ratio RH40:HP=1:2.25; and a series of mixed systems were obtained by mixing the oil phase and emulsion phase in different weight ratios, and the emulsification effect of the mixed systems were investigated. The mixing ratios of the oil phase and the emulsion phase are shown in Table 1.

TABLE 1

Experiments result I on Emulsification

| Oil phase (g) | Emulsion phase (g) | Water required to form microemulsion (g) | Emulsion state |
|---|---|---|---|
| 0.9 | 0.1 | — | Not emulsified, significantly visible oil droplets |
| 0.8 | 0.2 | — | Not emulsified, significantly visible oil droplets |
| 0.7 | 0.3 | — | Gray-white turbid substance, visible oil droplets |
| 0.6 | 0.4 | — | Gray-white turbid substance, visible oil droplets |
| 0.5 | 0.5 | — | Milky-white turbid substance |
| 0.4 | 0.6 | 748.6 | Microemulsion with blue light, high turbidity |
| 0.3 | 0.7 | 18.2 | Microemulsion with blue light |
| 0.2 | 0.8 | 6.1 | Microemulsion with slight blue light |
| 0.1 | 0.9 | 6.3 | Colorless and transparent microemulsion |

It can be seen from the experiments results in Table 1 that the amount of emulsion phase should be >60 wt. % (based on the total weight of oil phase and emulsion phase) to allow the self-emulsification of the mixed system composed of oil phase and emulsion phase. Further, in order to ensure the self-emulsification while also reduce the amount of emulsifier (i.e. RH40), the ratio of the amount of the oil phase to the emulsion phase were further optimized. The results are summarized in Table 2.

TABLE 2

Experiments results II on Emulsification

| Oil phase (g) | Emulsion phase (g) | Emulsion state after adding 100 g water to 1 g mixed system |
|---|---|---|
| 0.30 | 0.70 | Microemulsion with slight blue light |
| 0.31 | 0.69 | Microemulsion with slight blue light |
| 0.32 | 0.68 | Microemulsion with slight blue light |
| 0.33 | 0.67 | Microemulsion with blue light |
| 0.34 | 0.66 | Microemulsion with blue light |
| 0.35 | 0.65 | Microemulsion with blue light |
| 0.36 | 0.64 | Microemulsion with blue light, slight turbidity |
| 0.37 | 0.63 | Microemulsion with blue light, high turbidity |
| 0.38 | 0.62 | Microemulsion with blue light, high turbidity |
| 0.39 | 0.61 | Milky-white turbid substance |
| 0.40 | 0.60 | Milky-white turbid substance |

It can be seen from the experiments results in Table 2 that, when 100 g water was added, the total amount of the oil phase in the mixed system (i.e., the self-microemulsion system) composed of the oil phase and the emulsion phase should be less than or equal to 35 wt. %, and the total amount of the emulsion phase should be greater than or equal to 65 wt. %, such that a good emulsification of the self-microemulsion system can be obtained. In order to ensure the self-emulsification and also reduce the amount of emulsifier (i.e., RH40), the ratio of the weight percentages (based on the total weight of oil phase and emulsion phase) of oil phase to the emulsion phase in the self-microemulsion system can be 32 wt. %-35 wt. %:65 wt. %-68 wt. %, preferably 33 wt. %-35 wt. %:65 wt. %-67 wt. %, more preferably 35 wt. %:65 wt. %.

Experiment 2: Investigation of Drug Loading in Self-Microemulsion System 2.1. An oil phase was obtained by mixing CC and MCT in the weight ratio of CC:MCT=3.63:1, and an emulsion phase was obtained by mixing RH40 and HP in the weight ratio of RH40:HP=1:2.5. A self-microemulsion system for loading abiraterone acetate was obtained by mixing the oil phase and the emulsion phase in the weight ratio of 30 wt. %:70 wt. %. The self-microemulsion system was loaded with different amounts of abiraterone acetate (API), and the results are shown in Table 3.

TABLE 3

API Loading Experiment Results I

| Formulation | API content | API Placed at R.T. for 24 h | API Placed at 4° C. for 24 h | API capsule Placed at R.T. for 24 h | API capsule Placed at 4° C. for 24 h |
|---|---|---|---|---|---|
| Formulation 1 | 4.0 wt. % | Unprecipitated | Unprecipitated | Unprecipitated | Unprecipitated |
| Formulation 2 | 4.1 wt. % | Unprecipitated | Unprecipitated | Unprecipitated | Unprecipitated |
| Formulation 3 | 4.2 wt. % | Unprecipitated | Unprecipitated | Unprecipitated | Unprecipitated |
| Formulation 4 | 4.3 wt. % | Unprecipitated | Unprecipitated | Unprecipitated | Unprecipitated |
| Formulation 5 | 4.4 wt. % | Unprecipitated | Unprecipitated | Unprecipitated | Unprecipitated |
| Formulation 6 | 4.5 wt. % | Unprecipitated | Unprecipitated | Unprecipitated | Unprecipitated |
| Formulation 7 | 4.6 wt. % | Unprecipitated | Unprecipitated | Unprecipitated | Unprecipitated |
| Formulation 8 | 4.7 wt. % | Unprecipitated | Unprecipitated | Unprecipitated | Unprecipitated |
| Formulation 9 | 4.8 wt. % | Unprecipitated | Unprecipitated | Unprecipitated | Unprecipitated |
| Formulation 10 | 4.9 wt. % | Precipitated | Precipitated | Precipitated | Precipitated |
| Formulation 11 | 5.0 wt. % | Precipitated | Precipitated | Precipitated | Precipitated |

2.2. An oil phase was obtained by mixing CC and MCT in the weight ratio of CC:MCT=2.5:1, and an emulsion phase was obtained by mixing RH40 and HP in the weight ratio of RH40:HP=1:2.25. A self-microemulsion system for loading abiraterone acetate was obtained by mixing the oil phase and the emulsion phase in the weight ratio of 35 wt. %:65 wt. %. The self-microemulsion system was loaded with different amounts of abiraterone acetate (API), and the results are shown in Table 4.

TABLE 4

API Loading Experiment Results II

| Prescription | API content | API Placed at R.T. for 24 h | API Placed at 4° C. for 24 h | API capsule Placed at R.T. for 24 h | API capsule Placed at 4° C. for 24 h |
|---|---|---|---|---|---|
| Prescription 1 | 4.0 wt. % | Unprecipitated | Unprecipitated | Unprecipitated | Unprecipitated |
| Prescription 2 | 4.1 wt. % | Unprecipitated | Unprecipitated | Unprecipitated | Unprecipitated |
| Prescription 3 | 4.2 wt. % | Unprecipitated | Unprecipitated | Unprecipitated | Unprecipitated |
| Prescription 4 | 4.3 wt. % | Unprecipitated | Unprecipitated | Unprecipitated | Unprecipitated |
| Prescription 5 | 4.4 wt. % | Unprecipitated | Unprecipitated | Unprecipitated | Unprecipitated |
| Prescription 6 | 4.5 wt. % | Unprecipitated | Unprecipitated | Unprecipitated | Unprecipitated |
| Prescription 7 | 4.6 wt. % | Precipitated | Precipitated | Unprecipitated | Unprecipitated |
| Prescription 8 | 4.7 wt. % | Precipitated | Precipitated | Precipitated | Precipitated |
| Prescription 9 | 4.8 wt. % | Precipitated | Precipitated | Precipitated | Precipitated |
| Prescription 10 | 4.9 wt. % | Precipitated | Precipitated | Precipitated | Precipitated |
| Prescription 11 | 5.0 wt. % | Precipitated | Precipitated | Precipitated | Precipitated |

Referring to Table 3 and Table 4, it can be seen that the maximum effective drug loading capacity of abiraterone acetate of the self-microemulsion system provided by present embodiments is in the range of 4.5 wt. % to 4.8 wt. % (based on the total weight of API and self-microemulsion system). Besides, to maintain a proper dosage of the medicament loaded, the content of abiraterone acetate was determined to be no less than 4.3 wt. % upon calculation (an excessively low content of abiraterone acetate increases the dosage of medicament the subject has to take, leading to an increase in the amount of adjuvants as a carrier taken by the subject, and thus leading to a high risk of occurrence of toxic and side effects).

Example 1

The abiraterone acetate-containing composition comprises the following components:
abiraterone acetate: 1.118 portions by weight (comprising about 4.30 wt. % of the total weight of the composition);
glycerol monolinoleate: 6.722 portions by weight (comprising about 25.85 wt. % of the total weight of the composition);
medium chain triglyceride: 1.991 portions by weight (comprising about 7.66 wt. % of the total weight of the composition);
PEG-40 hydrogenated castor oil: 4.973 portions by weight (comprising about 19.13 wt. % of the total weight of the composition); and
2-(2-ethoxyethoxy)ethanol: 11.196 portions by weight (comprising about 43.06 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Example 2

The abiraterone acetate-containing composition comprises the following components:
abiraterone acetate: 1.170 portions by weight (comprising about 4.50 wt. % of the total weight of the composition);
glycerol monolinoleate: 6.704 portions by weight (comprising about 25.78 wt. % of the total weight of the composition);
medium chain triglyceride: 1.986 portions by weight (comprising about 7.64 wt. % of the total weight of the composition);
PEG-40 hydrogenated castor oil: 4.966 portions by weight (comprising about 19.10 wt. % of the total weight of the composition); and 2-(2-ethoxyethoxy)ethanol: 11.174 portions by weight (comprising about 42.98 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Example 3

The abiraterone acetate-containing composition comprises the following components:
abiraterone acetate: 1.248 portions by weight (comprising about 4.80 wt. % of the total weight of the composition);
glycerol monolinoleate: 6.683 portions by weight (comprising about 25.70 wt. % of the total weight of the composition);
medium chain triglyceride: 1.979 portions by weight (comprising about 7.61 wt. % of the total weight of the composition);
PEG-40 hydrogenated castor oil: 4.950 portions by weight (comprising about 19.04 wt. % of the total weight of the composition); and 2-(2-ethoxyethoxy)ethanol: 11.140 portions by weight (comprising about 42.85 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Example 4

The abiraterone acetate-containing composition comprises the following components:
abiraterone acetate: 1.170 portions by weight (comprising about 4.50 wt. % of the total weight of the composition);
glycerol monolinoleate: 6.523 portions by weight (comprising about 25.09 wt. % of the total weight of the composition);
medium chain triglyceride: 2.167 portions by weight (comprising about 8.33 wt. % of the total weight of the composition);
PEG-40 hydrogenated castor oil: 4.966 portions by weight (comprising about 19.10 wt. % of the total weight of the composition); and 2-(2-ethoxyethoxy)ethanol: 11.174 portions by weight (comprising about 42.98 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Example 5

The abiraterone acetate-containing composition comprises the following components:
abiraterone acetate: 1.170 portions by weight (comprising about 4.50 wt. % of the total weight of the composition);
glycerol monolinoleate: 6.207 portions by weight (comprising about 23.87 wt. % of the total weight of the composition);
medium chain triglyceride: 2.483 portions by weight (comprising about 9.55 wt. % of the total weight of the composition);
PEG-40 hydrogenated castor oil: 4.966 portions by weight (comprising about 19.10 wt. % of the total weight of the composition); and
2-(2-ethoxyethoxy)ethanol: 11.174 portions by weight (comprising about 42.98 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Example 6

The abiraterone acetate-containing composition comprises the following components:
abiraterone acetate: 1.170 portions by weight (comprising about 4.50 wt. % of the total weight of the composition);
glycerol monolinoleate: 6.760 portions by weight (comprising about 26.00 wt. % of the total weight of the composition);
medium chain triglyceride: 1.930 portions by weight (comprising about 7.42 wt. % of the total weight of the composition);
PEG-40 hydrogenated castor oil: 4.966 portions by weight (comprising about 19.10 wt. % of the total weight of the composition); and
2-(2-ethoxyethoxy)ethanol: 11.174 portions by weight (comprising about 42.98 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Example 7

The abiraterone acetate-containing composition comprises the following components:
abiraterone acetate: 1.170 portions by weight (comprising about 4.50 wt. % of the total weight of the composition);
glycerol monolinoleate: 6.704 portions by weight (comprising about 25.78 wt. % of the total weight of the composition);
medium chain triglyceride: 1.986 portions by weight (comprising about 7.64 wt. % of the total weight of the composition);
PEG-40 hydrogenated castor oil: 4.747 portions by weight (comprising about 18.26 wt. % of the total weight of the composition); and 2-(2-ethoxyethoxy)ethanol: 11.393 portions by weight (comprising about 43.82 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Example 8

The abiraterone acetate-containing composition comprises the following components:
abiraterone acetate: 1.170 portions by weight (comprising about 4.50 wt. % of the total weight of the composition);
glycerol monolinoleate: 6.704 portions by weight (comprising about 25.78 wt. % of the total weight of the composition);
medium chain triglyceride: 1.986 portions by weight (comprising about 7.64 wt. % of the total weight of the composition);
PEG-40 hydrogenated castor oil: 4.638 portions by weight (comprising about 17.84 wt. % of the total weight of the composition); and
2-(2-ethoxyethoxy)ethanol: 11.502 portions by weight (comprising about 44.24 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Example 9

The abiraterone acetate-containing composition comprises the following components:
abiraterone acetate: 1.170 portions by weight (comprising about 4.50 wt. % of the total weight of the composition);
glycerol monolinoleate: 6.322 portions by weight (comprising about 24.32 wt. % of the total weight of the composition);
medium chain triglyceride: 1.872 portions by weight (comprising about 7.20 wt. % of the total weight of the composition);
PEG-40 hydrogenated castor oil: 4.966 portions by weight (comprising about 19.10 wt. % of the total weight of the composition); and 2-(2-ethoxyethoxy)ethanol: 11.670 portions by weight (comprising about 44.88 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Example 10

The abiraterone acetate-containing composition comprises the following components:
abiraterone acetate: 1.170 portions by weight (comprising about 4.50 wt. % of the total weight of the composition);
glycerol monolinoleate: 6.130 portions by weight (comprising about 23.58 wt. % of the total weight of the composition);
medium chain triglyceride: 1.816 portions by weight (comprising about 6.98 wt. % of the total weight of the composition);
PEG-40 hydrogenated castor oil: 4.966 portions by weight (comprising about 19.10 wt. % of the total weight of the composition); and
2-(2-ethoxyethoxy)ethanol: 11.918 portions by weight (comprising about 45.84 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Example 11

The abiraterone acetate-containing composition comprises the following components:
abiraterone acetate: 1.170 portions by weight (comprising about 4.50 wt. % of the total weight of the composition);
glycerol monolinoleate: 5.747 portions by weight (comprising about 22.10 wt. % of the total weight of the composition);
medium chain triglyceride: 1.702 portions by weight (comprising about 6.55 wt. % of the total weight of the composition);
PEG-40 hydrogenated castor oil: 4.966 portions by weight (comprising about 19.10 wt. % of the total weight of the composition); and
2-(2-ethoxyethoxy)ethanol: 12.415 portions by weight (comprising about 47.75 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Comparative Example 1

The abiraterone acetate-containing composition comprises the following components:
abiraterone acetate: 1.170 portions by weight (comprising about 7.11 wt. % of the total weight of the composition);
glycerol monolinoleate: 4.136 portions by weight (comprising about 25.13 wt. % of the total weight of the composition);
medium chain triglyceride: 2.632 portions by weight (comprising about 15.99 wt. % of the total weight of the composition);
PEG-40 hydrogenated castor oil: 3.816 portions by weight (comprising about 23.19 wt. % of the total weight of the composition); and
2-(2-ethoxyethoxy)ethanol: 4.704 portions by weight (comprising about 28.58 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Comparative Example 2

The abiraterone acetate-containing composition comprises the following components:
abiraterone acetate: 1.170 portions by weight (comprising about 8.78 wt. % of the total weight of the composition);
glycerol monolinoleate: 4.136 portions by weight (comprising about 31.05 wt. % of the total weight of the composition);
medium chain triglyceride: 2.632 portions by weight (comprising about 19.76 wt. % of the total weight of the composition);
PEG-40 hydrogenated castor oil: 3.816 portions by weight (comprising about 28.64 wt. % of the total weight of the composition); and
2-(2-ethoxyethoxy)ethanol: 1.568 portions by weight (comprising about 11.77 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)

ethanol was added to form a transparent and homogeneous self-emulsification solution, namely the abiraterone acetate-containing composition.

Comparative Example 3

The abiraterone acetate-containing composition comprises the following components:
abiraterone acetate: 1.170 portions by weight (comprising about 4.03 wt. % of the total weight of the composition);
glycerol monolinoleate: 4.136 portions by weight (comprising about 14.26 wt. % of the total weight of the composition);
medium chain triglyceride: 2.632 portions by weight (comprising about 9.08 wt. % of the total weight of the composition);
PEG-40 hydrogenated castor oil: 3.816 portions by weight (comprising about 13.16 wt. % of the total weight of the composition); and
2-(2-ethoxyethoxy)ethanol: 17.248 portions by weight (comprising about 59.47 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Comparative Example 4

The abiraterone acetate-containing composition comprises the following components:
abiraterone acetate: 1.170 portions by weight (comprising about 2.45 wt. % of the total weight of the composition);
glycerol monolinoleate: 4.136 portions by weight (comprising about 8.65 wt. % of the total weight of the composition);
medium chain triglyceride: 2.632 portions by weight (comprising about 5.50 wt. % of the total weight of the composition);
PEG-40 hydrogenated castor oil: 3.816 portions by weight (comprising about 7.98 wt. % of the total weight of the composition); and
2-(2-ethoxyethoxy)ethanol: 36.064 portions by weight (comprising about 75.42 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Comparative Example 5

The abiraterone acetate-containing composition comprises the following components:
abiraterone acetate: 1.300 portions by weight (comprising about 5.0 wt. % of the total weight of the composition);
glycerol monolinoleate: 6.667 portions by weight (comprising about 25.64 wt. % of the total weight of the composition);
medium chain triglyceride: 1.975 portions by weight (comprising about 7.60 wt. % of the total weight of the composition);
PEG-40 hydrogenated castor oil: 4.940 portions by weight (comprising about 19.00 wt. % of the total weight of the composition); and
2-(2-ethoxyethoxy)ethanol: 11.118 portions by weight (comprising about 42.76 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Comparative Example 6

The abiraterone acetate-containing composition comprises the following components:
abiraterone acetate: 1.170 portions by weight (comprising about 4.50 wt. % of the total weight of the composition);
glycerol monolinoleate: 6.822 portions by weight (comprising about 26.24 wt. % of the total weight of the composition);
medium chain triglyceride: 1.868 portions by weight (comprising about 7.18 wt. % of the total weight of the composition);
PEG-40 hydrogenated castor oil: 4.966 portions by weight (comprising about 19.10 wt. % of the total weight of the composition); and
2-(2-ethoxyethoxy)ethanol: 11.174 portions by weight (comprising about 42.98 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Comparative Example 7

The abiraterone acetate-containing composition comprises the following components:
abiraterone acetate: 1.170 portions by weight (comprising about 4.50 wt. % of the total weight of the composition);
glycerol monolinoleate: 6.704 portions by weight (comprising about 25.78 wt. % of the total weight of the composition);
medium chain triglyceride: 1.986 portions by weight (comprising about 7.64 wt. % of the total weight of the composition);
PEG-40 hydrogenated castor oil: 4.547 portions by weight (comprising about 17.49 wt. % of the total weight of the composition); and
2-(2-ethoxyethoxy)ethanol: 11.593 portions by weight (comprising about 44.59 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Comparative Example 8

The abiraterone acetate-containing composition comprises the following components:
abiraterone acetate: 1.170 portions by weight (comprising about 4.50 wt. % of the total weight of the composition);
glycerol monolinoleate: 5.747 portions by weight (comprising about 22.10 wt. % of the total weight of the composition);
medium chain triglyceride: 1.702 portions by weight (comprising about 6.55 wt. % of the total weight of the composition);
PEG-40 hydrogenated castor oil: 5.348 portions by weight (comprising about 20.57 wt. % of the total weight of the composition); and
2-(2-ethoxyethoxy)ethanol: 12.033 portions by weight (comprising about 46.28 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Comparative Example 9

The abiraterone acetate-containing composition comprises the following components:
abiraterone acetate: 1.170 portions by weight (comprising about 4.50 wt. % of the total weight of the composition);
glycerol monolinoleate: 7.087 portions by weight (comprising about 27.26 wt. % of the total weight of the composition);
medium chain triglyceride: 2.100 portions by weight (comprising about 8.08 wt. % of the total weight of the composition);
PEG-40 hydrogenated castor oil: 4.813 portions by weight (comprising about 18.51 wt. % of the total weight of the composition); and
2-(2-ethoxyethoxy)ethanol: 10.830 portions by weight (comprising about 41.65 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Comparative Example 10

The abiraterone acetate-containing composition comprises the following components:
abiraterone acetate: 1.170 portions by weight (comprising about 4.50 wt. % of the total weight of the composition);
glycerol monolinoleate: 6.130 portions by weight (comprising about 23.58 wt. % of the total weight of the composition);
medium chain triglyceride: 1.816 portions by weight (comprising about 6.98 wt. % of the total weight of the composition);
PEG-40 hydrogenated castor oil: 5.195 portions by weight (comprising about 19.98 wt. % of the total weight of the composition); and
2-(2-ethoxyethoxy)ethanol: 11.689 portions by weight (comprising about 44.96 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Comparative Example 11

The abiraterone acetate-containing composition comprises the following components:
abiraterone acetate: 1.170 portions by weight (comprising about 4.50 wt. % of the total weight of the composition);
glycerol monolinoleate: 6.704 portions by weight (comprising about 25.78 wt. % of the total weight of the composition);
medium chain triglyceride: 1.986 portions by weight (comprising about 7.64 wt. % of the total weight of the composition);
PEG-40 hydrogenated castor oil: 5.124 portions by weight (comprising about 19.71 wt. % of the total weight of the composition); and
2-(2-ethoxyethoxy)ethanol: 11.016 portions by weight (comprising about 42.37 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy)ethanol was added to form a transparent and homogeneous self-emulsification solution, namely the abiraterone acetate-containing composition.

Comparative Example 12

The abiraterone acetate-containing composition comprises the following components:
abiraterone acetate: 1.170 portions by weight (comprising about 4.50 wt. % of the total weight of the composition);
glycerol monolinoleate: 5.364 portions by weight (comprising about 20.63 wt. % of the total weight of the composition);
medium chain triglyceride: 1.588 portions by weight (comprising about 6.11 wt. % of the total weight of the composition);
PEG-40 hydrogenated castor oil: 5.501 portions by weight (comprising about 21.16 wt. % of the total weight of the composition); and
2-(2-ethoxyethoxy)ethanol: 12.377 portions by weight (comprising about 47.60 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Comparative Example 13

The abiraterone acetate-containing composition comprises the following components:
abiraterone acetate: 1.170 portions by weight (comprising about 4.50 wt. % of the total weight of the composition);
glycerol monolinoleate: 6.134 portions by weight (comprising about 23.59 wt. % of the total weight of the composition);
medium chain triglyceride: 2.556 portions by weight (comprising about 9.83 wt. % of the total weight of the composition);
PEG-40 hydrogenated castor oil: 4.966 portions by weight (comprising about 19.10 wt. % of the total weight of the composition); and
2-(2-ethoxyethoxy)ethanol: 11.174 portions by weight (comprising about 42.98 wt. % of the total weight of the composition).

The preparation process is as follows. Glycerol monolinoleate, medium chain triglyceride, PEG-40 hydrogenated castor oil were taken in proportion, stirred and mixed homogeneously, followed by adding abiraterone acetate in dark place. After being fully dissolved, 2-(2-ethoxyethoxy) ethanol was added to form a transparent and homogeneous self-emulsification solution, namely the abiraterone acetate-containing composition.

Experimental Example 1

Abiraterone acetate-containing compositions were obtained according to the amount configurations of the above-mentioned Examples 1-11 and Comparative examples 1-13. The composition proportion of the composition of each Example is shown in Table 5. Each abiraterone acetate-containing composition is subjected to stability test. Specifically, the abiraterone acetate-containing compositions obtained in Examples 1-11 and Comparative examples 1-13 were placed for 24 h under conditions of: at room temperature; at 4° C.; at room temperature with the addition of 10 wt. % water; and at room temperature with the addition of 15 wt. % water. The stability of each abiraterone acetate-containing composition was observed and the results are shown in Table 6.

TABLE 5

Composition proportions of abiraterone acetate-containing compositions

| | API (%) | CC (%) | MCT (%) | RH40 (%) | HP (%) | Oil phase/ Emulsion phase | CC/MCT | RH40/HP |
|---|---|---|---|---|---|---|---|---|
| Example 1 | 4.30 | 25.85 | 7.66 | 19.13 | 43.06 | 35%:65% | 3.38:1 | 1:2.25 |
| Example 2 | 4.50 | 25.78 | 7.64 | 19.10 | 42.98 | 35%:65% | 3.38:1 | 1:2.25 |
| Example 3 | 4.80 | 25.70 | 7.61 | 19.04 | 42.85 | 35%:65% | 3.38:1 | 1:2.25 |
| Example 4 | 4.50 | 25.09 | 8.33 | 19.10 | 42.98 | 35%:65% | 3.01:1 | 1:2.25 |
| Example 5 | 4.50 | 23.87 | 9.55 | 19.10 | 42.98 | 35%:65% | 2.50:1 | 1:2.25 |
| Example 6 | 4.50 | 26.00 | 7.42 | 19.10 | 42.98 | 35%:65% | 3.50:1 | 1:2.25 |
| Example 7 | 4.50 | 25.78 | 7.64 | 18.26 | 43.82 | 35%:65% | 3.38:1 | 1:2.40 |
| Example 8 | 4.50 | 25.78 | 7.64 | 17.84 | 44.24 | 35%:65% | 3.38:1 | 1:2.48 |
| Example 9 | 4.50 | 24.32 | 7.20 | 19.10 | 44.88 | 33%:67% | 3.38:1 | 1:2.35 |
| Example 10 | 4.50 | 23.58 | 6.98 | 19.10 | 45.84 | 32%:68% | 3.38:1 | 1:2.40 |
| Example 11 | 4.50 | 22.10 | 6.55 | 19.10 | 47.75 | 30%:70% | 3.38:1 | 1:2.50 |
| Comparative example 1 | 7.11 | 25.13 | 15.99 | 23.19 | 28.58 | 44%:56% | 1.571:1 | 1:2.33 |
| Comparative example 2 | 8.78 | 31.05 | 19.76 | 28.64 | 11.77 | 56%:44% | 1.571:1 | 1:0.41 |
| Comparative example 3 | 4.03 | 14.26 | 9.08 | 13.16 | 59.47 | 24%:76% | 1.571:1 | 1:4.52 |
| Comparative example 4 | 2.45 | 8.65 | 5.50 | 7.98 | 75.42 | 15%:85% | 1.571:1 | 1:9.45 |
| Comparative example 5 | 5.00 | 25.64 | 7.60 | 19.00 | 42.76 | 35%:65% | 3.38:1 | 1:2.25 |
| Comparative example 6 | 4.50 | 26.24 | 7.18 | 19.10 | 42.98 | 35%:65% | 3.65:1 | 1:2.25 |
| Comparative example 7 | 4.50 | 25.78 | 7.64 | 17.49 | 44.59 | 35%:65% | 3.38:1 | 1:2.55 |
| Comparative example 8 | 4.50 | 22.10 | 6.55 | 20.57 | 46.28 | 30%:70% | 3.38:1 | 1:2.25 |
| Comparative example 9 | 4.50 | 27.26 | 8.08 | 18.51 | 41.65 | 37%:63% | 3.38:1 | 1:2.25 |
| Comparative example 10 | 4.50 | 23.58 | 6.98 | 19.98 | 44.96 | 32%:68% | 3.38:1 | 1:2.25 |
| Comparative example 11 | 4.50 | 25.78 | 7.64 | 19.71 | 42.37 | 35%:65% | 3.38:1 | 1:2.15 |
| Comparative example 12 | 4.50 | 20.63 | 6.11 | 21.16 | 47.60 | 28%:72% | 3.38:1 | 1:2.25 |
| Comparative example 13 | 4.5 | 23.59 | 9.83 | 19.10 | 42.98 | 35%:65% | 2.40:1 | 1:2.25 |

Note:
The value of oil phase or emulsion phase is represented by the percentages of the oil phase or the emulsion phase based on the total weight of the oil phase and the emulsion phase.

TABLE 6

Investigation on the stability of the abiraterone acetate-containing compositions

| | R.T. | 4° C. | 10 wt. % water of the total weight of composition added | 15 wt. % water of the total weight of composition added |
|---|---|---|---|---|
| Example 1 | Unprecipitated | Unprecipitated | Unprecipitated | Unprecipitated |
| Example 2 | Unprecipitated | Unprecipitated | Unprecipitated | Unprecipitated |
| Example 3 | Unprecipitated | Unprecipitated | Unprecipitated | Unprecipitated |
| Example 4 | Unprecipitated | Unprecipitated | Unprecipitated | Unprecipitated |
| Example 5 | Unprecipitated | Unprecipitated | Unprecipitated | Unprecipitated |
| Example 6 | Unprecipitated | Unprecipitated | Unprecipitated | Unprecipitated |
| Example 7 | Unprecipitated | Unprecipitated | Slightly precipitated | Slightly precipitated |
| Example 8 | Unprecipitated | Unprecipitated | Slightly precipitated | Slightly precipitated |
| Example 9 | Unprecipitated | Unprecipitated | Unprecipitated | Unprecipitated |
| Example 10 | Unprecipitated | Unprecipitated | Unprecipitated | Unprecipitated |
| Example 11 | Unprecipitated | Unprecipitated | Unprecipitated | Unprecipitated |
| Comparative example 1 | Unprecipitated | Precipitated | Precipitated | Precipitated |
| Comparative example 2 | Unprecipitated | Precipitated | Precipitated | Precipitated |
| Comparative example 3 | Unprecipitated | Unprecipitated | Layers separated | Layers separated |
| Comparative example 4 | Unprecipitated | Unprecipitated | Layers separated | Layers separated |
| Comparative example 5 | API largely precipitated | API largely precipitated | API largely precipitated | API largely precipitated |
| Comparative example 6 | Unprecipitated | Unprecipitated | Oil droplets precipitated | Oil droplets precipitated |
| Comparative example 7 | API precipitated | API precipitated | API precipitated | API precipitated |
| Comparative example 8 | Unprecipitated | Unprecipitated | Layers separated | Layers separated |
| Comparative example 9 | Unprecipitated | Unprecipitated | Oil droplets precipitated | Oil droplets precipitated |
| Comparative example 10 | Unprecipitated | Unprecipitated | Layers separated | Layers separated |
| Comparative example 11 | Unprecipitated | Unprecipitated | Layers separated | Layers separated |
| Comparative example 12 | API precipitated | API precipitated | API precipitated | API precipitated |
| Comparative example 13 | API precipitated | API precipitated | API precipitated | API precipitated |

In Comparative example 1, the API content was too high and exceeded the maximum drug loading capacity of the system, rendering the carrier and adjuvants precipitated and the system being turbid. In Comparative example 2, the HP content was too low while the API content was too high, resulting in the precipitation of API and the appearance of medicament particle crystals at the bottom of the composition. Further, API was precipitated in both Comparative example 1 and Comparative example 2 after adding a small amount of water. In general, the prepared pharmaceutical composition tends to absorb moisture during subsequent long-term storage, resulting in an increase in moisture content. In Comparative example 5, the excessively high API content results in the formation of a large amount of API precipitation. In comparative example 6, the excessive proportion of CC lead to an excessive amount of oil phase, resulting in the precipitation of oil droplets under humid or over-humid conditions (i.e. after adding a small amount of water). Comparative example 7 comprises a large proportion of HP that is hydrophilic. Accordingly, under humid or over-humid conditions, after being dispersed in water, some medicament could not be completely dissolved and was precipitated. Besides, the excessively high content of HP leads to the increase of toxic and side effects of medicaments. Comparative examples 8, 10 and 11 have a low content of HP, and cannot achieve a satisfying emulsification effect (wherein Comparative example 11 comprises an excessively low content of HP and failed to form microemulsion). Further, these compositions were layered under humid or over-humid conditions. In Comparative example 9, the content of the emulsion phase was so low that the microemulsion could not be formed, while the content of the oil phase was too high that a large number of oil droplets were precipitated under humid or over-humid conditions. In Comparative example 12, due to the lower oil phase content and the higher emulsion phase content, the content of HP, which is hydrophilic, was relatively high. Accordingly, after being dispersed in water, some medicament could not be completely dissolved and was precipitated. In comparative example 13, due to the excessively low content of CC, the resulting self-microemulsion system has a low loading capacity of API, resulting in the precipitation of API. Moreover, in Examples 7 and 8, with a specific ratio of oil phase and emulsion phase, the percentage of HP in the emulsion phase was slightly high, making the HP content in these Examples slightly high. HP is hydrophilic, and thus trace amount of medicament, after being dispersed in water under humid or over-humid conditions, could not be completely dissolved and was precipitated.

Further, the self-microemulsion systems of Example 2 and Comparative examples 1-4 after emulsification were placed under a temperature of 30° C.±5° C. for 24 h and 48 h, respectively. The stability of the self-microemulsion systems were observed and summarized in Table 7.

TABLE 7

|  | Example 2 | Comparative example 1 | Comparative example 2 | Comparative example 3 | Comparative example 4 |
|---|---|---|---|---|---|
| 24 h | No obvious change was observed | | | | |
| 48 h | No obvious change was observed | | | Oil droplets precipitated | Oil droplets precipitated |

Referring to the Table 7 above, it can be seen that there was cargo (API) precipitated in both Comparative examples 3 and 4 after forming the self-microemulsion system, which indicates that both the self-microemulsion systems have poor long-term stabilities. Due to the low oil phase content in Comparative example 4 was low, co-emulsifier (HP) was added in a content of more than 70% in order to form a transparent solution. However, the co-emulsifier was hydrophilic, and after dispersing in water, part of API could not be completely dissolved and was precipitated. Besides, the excessively high content of the co-emulsifier leads to an increase of toxic and side effects of the medicament. The oil phase content in Comparative example 3 was relatively low, and accordingly leaded to large particles after emulsification, which hinders the subsequent absorption. Besides, there was drug precipitation after a period of storage.

Application Example 1

Pharmacokinetic experiments were performed on the abiraterone acetate-containing composition prepared according to the present disclosure and Example 1 in the prior art document WO2021057042 (hereinafter referred to as "Comparative example 14").

Experiment methods and subjects: 6 healthy beagle dogs, randomly divided into 3 groups with 2 dogs in each group; interperiodic washout period being 3 days.

The experiments were designed as fasting experiment and postprandial experiment.

Fasting test: fasted for 10 hours before the experiment; administered on an empty stomach, and fed 4 hours after administration.

Postprandial test: fasted for 10 hours before the experiment, and fed a high-fat meal followed by administering (feeding and administering were completed within 30 minutes).

The experiment was carried out with the abiraterone acetate-containing capsules provided in the examples of the present invention and the Comparative example 14, wherein a single capsule contains 50 mg of abiraterone acetate.

Sampling design: 2 ml blood sample was collected at each of 15 min, 30 min, 1 h, 1.5 h, 2.0 h, 2.5 h, 3 h, 4 h, 6 h, 8 h, 10 h, 12 h, and 24 h after administering, and the plasma was separated by centrifugation. The results of the pharmacokinetic experiments of the abiraterone acetate-containing compositions of the present invention being prepared into capsule are shown in Table 8.

TABLE 8

Results of pharmacokinetic parameters

| Examples | Average $AUC_{last}$ in fasting test on beagle dogs (h·ng/mL) | Average $AUC_{last}$ in postprandial test on beagle dogs (h·ng/mL) | Bioavailability of oral administration in fasting test/Comparative example 14 | $AUC_{last}$ of postprandial test/$AUC_{last}$ of fasting test |
|---|---|---|---|---|
| Comparative example 14 | 553.29 | 669.2 | — | 1.21 |
| Example 1 | 752.41 | 855.03 | 135.99% | 1.14 |
| Example 2 | 756.39 | 857.14 | 136.71% | 1.13 |
| Example 3 | 788.72 | 847.63 | 142.55% | 1.07 |
| Example 4 | 769.1 | 822.52 | 139.00% | 1.07 |
| Example 5 | 723.85 | 789.18 | 130.83% | 1.09 |
| Example 6 | 774.04 | 848.26 | 139.90% | 1.10 |
| Example 7 | 781.58 | 739.48 | 141.26% | 0.95 |
| Example 8 | 765.03 | 755.97 | 138.27% | 0.99 |
| Example 9 | 773.95 | 814.28 | 139.88% | 1.05 |
| Example 10 | 745.37 | 833.41 | 134.72% | 1.12 |
| Example 11 | 777.18 | 808.75 | 140.47% | 1.04 |

As seen in Table 8, the oral bioavailability of abiraterone acetate capsules of Example 2 administered orally to Beagle on an empty stomach was 136.71% of the oral bioavailability of abiraterone acetate capsule of Comparison example 14. This indicates that, comparing with Comparative example 14, the oral bioavailability of the abiraterone acetate pharmaceutical composition of the present invention increased to about 1.36 times, and have a low inter-individual variability in peak time, peak concentration and absorption level of the medicaments. When the abiraterone acetate capsule of Comparative example 14 (containing 50 mg of abiraterone acetate) were administered after fasting or high-fat meals, there was no significant difference in peak time in Beagle, and the oral bioavailability in postprandial test was 1.21 times that of the preprandial test (i.e. the fasting test). When abiraterone acetate capsule of Example 2 (containing 50 mg of abiraterone acetate) were administered after fasting and high-fat meals, there was no significant difference in peak time in Beagle, and the oral bioavailability in postprandial test was only 1.13 times that of the preprandial test. It can be seen that the abiraterone acetate capsules provided by the present invention further reduced the differences between preprandial and postprandial.

Furthermore, as seen in Table 8, the postprandial oral bioavailability of abiraterone acetate capsules provided by the present invention ranges from 0.95 to 1.14 times that of the preprandial oral bioavailability, indicating the difference between preprandial and postprandial was reduced. Meanwhile, the oral bioavailability of the present capsules for Beagle in a fasting test is 130.83%-142.55% of the oral bioavailability of the abiraterone acetate capsule of Comparative example 14, indicating that the abiraterone acetate capsules provided by the present invention further improved the oral bioavailability under fasting.

Application Example 2

1. Tissue Distribution of Abiraterone Acetate Capsules 1.1 Administration

Male rats were randomly divided into groups with each group 9 rats. The specific administration scheme is as follows.

9 male rats in group 1 were orally administered with the innovator drug Zytiga at a dosage of 500 mg;

36 male rats in groups 2-5 were orally administered with the abiraterone acetate capsules prepared according the present disclosure (Comparative example 14, Example 2, Example 6, and Example 10) at a dosage of 50 mg.

1.2 Sample Collection and Treatment

Three rats were sacrificed at each time point of 0.5 h, 2 h and 4 h, respectively, after gavage administration of the innovator drug Zytiga, and three rats were sacrificed at each time point of 0.5 h, 2 h and 4 h, respectively, after gavage administration of the abiraterone acetate capsule. 0.5 mL of venous blood was collected, and then the dissection was quickly carried out to take heart, liver, spleen, lung, kidney, stomach, intestine, sputum, brain, spine, spinal fluid, nerve, thymus, lymph nodes, arterial wall, pancreas, gallbladder, prostate, testis, thyroid, adrenal gland, hypothalamus, pituitary gland, eye, ear, bladder, muscle, skin, white blood cells, bone, cartilage, joint tissue, synovial fluid, adipose tissue, and the like. The taken tissues were washed with normal saline to remove the surface blood stains, then dried with filter paper and weighed respectively. Besides, fecal samples are collected from the rat intestines and weighed to determine the amount of unabsorbed medicament.

The collected blood samples were anticoagulated with sodium heparin and centrifuged at 3500 rpm for 10 min at 2-8° C. within 1 h after collection. The separated plasma was stored at −80° C. in a refrigerator for subsequent tests, and the lymphocytes and erythrocytes at the bottom are also recovered and stored at −80° C. in a refrigerator for subsequent tests.

A certain amount (about 0.2 g) of each tissue sample was taken, and 3 mL of normal saline was added for every 1 g tissue. The mixture was fully stir-crushed with an electric homogenizer under an ice bath, and stored in a refrigerator at −80° C. for subsequent tests. The rest of the tissue that were not homogenized were recovered and stored in a −80° C. refrigerator.

The procedure of the sample collection and treatment was performed in dark place.

1.3 Sample Detection

LC-MS/MS method was used to detect the concentration of abiraterone acetate in plasma samples, tissue samples (including testis and prostate) and fecal samples of rats respectively. The results are summarized in Tables 9-10 below.

TABLE 9

Detection results of the ratios of rat tissue samples/plasma samples

| Concentration of abiraterone acetate in tissue sample/in plasma sample | Medicaments | 0.5 h | 2 h | 4 h |
|---|---|---|---|---|
| Ratio of concentration in testis sample to that in plasma sample | Innovator drug Zytiga | 0.0468 | 0.1161 | 0.6621 |
| | Comparative example 14 | 0.0556 | 0.2518 | 1.5456 |
| | Example 2 | 0.1342 | 0.6792 | 2.3424 |
| | Example 6 | 0.1324 | 0.6270 | 1.8209 |
| | Example 10 | 0.1328 | 0.4931 | 2.3086 |
| Ratio of concentration in prostate sample to that in plasma sample | Innovator drug Zytiga | 0.08799 | 3.5926 | 6.4445 |
| | Comparative example 14 | 0.3779 | 10.2045 | 15.4813 |
| | Example 2 | 2.7474 | 16.5699 | 17.2236 |
| | Example 6 | 1.4594 | 11.7562 | 16.4445 |
| | Example 10 | 2.5592 | 14.5396 | 16.9481 |

Referring to the results in Table 9, taking the concentration of abiraterone acetate in plasma samples as a baseline, the testicular and prostate samples taken from the rats that administered with the abiraterone acetate compositions of the present disclosure (Comparison example 14, Example 2, Example 6, Example 10) showed high medicament concentrations, indicating that abiraterone aggregated in the testis and prostate. Abiraterone acetate with a high concentration in specific local tissues facilitates it accessing to the target location and producing better efficacy.

TABLE 10

Detection results of abiraterone concentration in fecal samples of rats

| | Medicaments | 4 h |
|---|---|---|
| Abiraterone concentration in fecal samples | Innovator drug Zytiga | 13430 |
| | Comparative example 14 | 163.1 |
| | Example 2 | 50.7 |
| | Example 6 | 61.61 |
| | Example 10 | 32.77 |

The results in Table 10 shows that, after 4 h of administration, the concentrations of abiraterone in the fecal samples of rats that administered with the abiraterone acetate composition of the examples of the present invention were significantly lower than that in equal weight of fecal samples of rats given the control medicament, indicating that more abiraterone in the abiraterone acetate composition of the examples of the present invention was absorbed.

I claim:

1. An abiraterone acetate-containing composition, wherein the composition comprises abiraterone acetate and a self-microemulsion system, wherein the ratio of the weight percentages of abiraterone acetate to the self-microemulsion system is 4.3%-4.8% : 95.2%-95.7%; and the self-microemulsion system comprises an oil phase and an emulsion phase, and the ratio of the weight percentages of the oil phase and the emulsion phase is 30%-38% : 62%-70%; the oil phase comprises glycerol monolinoleate and medium chain triglycerides; the weight ratio of glycerol monolinoleate to medium chain triglycerides is 2.5-3.63:1; the emulsion phase comprises PEG-40 hydrogenated castor oil and 2-(2-ethoxyethoxy)ethanol; and the weight ratio of PEG-40 hydrogenated castor oil to 2-(2-ethoxyethoxy)ethanol in the emulsion phase is 1:2.25-2.5.

2. The composition according to claim 1, wherein the ratio of the weight percentages of abiraterone acetate to the self-microemulsion system is 4.4%-4.6% : 95.4%-95.6%.

3. The composition according to claim 1, wherein the ratio of the weight percentages of the oil phase and the emulsion phase is 31%-35% : 65%-69%.

4. The composition according to claim 3, wherein the ratio of the weight percentages of the oil phase and the emulsion phase is 32%-34% : 66%-68%.

5. The composition according to claim 1, wherein the weight ratio of glycerol monolinoleate to medium chain triglycerides is 2.8-3.5:1; and/or the weight ratio of PEG-40 hydrogenated castor oil to 2-(2-ethoxyethoxy)ethanol phase is 1:2.28-2.45.

6. The composition according to claim 1, wherein the weight ratio of glycerol monolinoleate to medium chain triglycerides is 3.0-3.4:1; and/or the weight ratio of PEG-40 hydrogenated castor oil to 2-(2-ethoxyethoxy)ethanol is 1:2.25-2.4.

7. The composition according to claim 1, wherein the composition comprises the following components:

abiraterone acetate: 4.3-4.8 wt. %;
glycerol monolinoleate: 21.4-26.2 wt. %;
medium chain triglycerides: 6.2-9.6 wt. %;

PEG-40 hydrogenated castor oil: 17.7-19.7 wt. %; and
2-(2-ethoxyethoxy)ethanol: 42.8-47.8 wt. %.

8. The composition according to claim 1, wherein the composition comprises the following components:
abiraterone acetate: 4.4-4.6 wt. %;
glycerol monolinoleate: 22.0-26.0 wt. %;
medium chain triglycerides: 6.8-8.8 wt. %;
PEG-40 hydrogenated castor oil: 18.5-19.5 wt. %; and
2-(2-ethoxyethoxy)ethanol: 43.0-47.2 wt. %.

9. The composition according to claim 7, wherein the composition further comprises an antioxidant and/or a preservative, wherein the antioxidant and/or the preservative comprise 0.005%-0.1% of the total weight of the composition.

10. A capsule comprising the abiraterone acetate-containing composition according to claim 1.

11. A method for treating prostate cancer, comprising administering the abiraterone acetate-containing composition according to claim 1 to a subject in need thereof.

\* \* \* \* \*